United States Patent [19]

Jacobs

[11] Patent Number: 4,462,394
[45] Date of Patent: Jul. 31, 1984

[54] INTRAMEDULLARY CANAL SEAL FOR CEMENT PRESSURIZATION

[75] Inventor: Carl H. Jacobs, New London, Conn.

[73] Assignee: Howmedica, Inc., New York, N.Y.

[21] Appl. No.: 374,533

[22] Filed: May 3, 1982

[51] Int. Cl.³ ............................................. A61F 5/04
[52] U.S. Cl. ............................ 128/92 C; 128/92 BC;
128/92 E; 128/344
[58] Field of Search ................. 128/92 R, 92 E, 92 C,
128/92 CA, 303 R, 344, 92 BC; 604/96–103

[56] References Cited

U.S. PATENT DOCUMENTS

| | | | |
|---|---|---|---|
| 3,223,083 | 12/1965 | Cobey | 128/92 R |
| 3,225,760 | 12/1965 | DiCosola | 128/83 |
| 3,255,747 | 6/1966 | Cochran et al. | 128/92 R |
| 3,707,146 | 12/1972 | Cook et al. | 128/2 R |
| 3,889,665 | 6/1975 | Ling et al. | 128/92 R |
| 4,160,446 | 7/1979 | Barrington | 604/96 |
| 4,213,461 | 7/1980 | Pevsner | 604/96 |
| 4,274,163 | 6/1981 | Malcom et al. | 3/1.91 |
| 4,313,434 | 2/1982 | Segal | 128/92 BC |
| 4,328,056 | 5/1982 | Snooks | 604/96 |
| 4,338,925 | 7/1982 | Miller | 128/92 E |
| 4,340,046 | 7/1982 | Cox | 604/96 |
| 4,341,691 | 7/1982 | Anuta | 128/92 R |
| 4,357,716 | 11/1982 | Brown | 3/1.913 |
| 4,364,394 | 12/1982 | Wilkinson | 604/96 |
| 4,369,772 | 1/1983 | Miller | 128/92 R |
| 4,399,814 | 8/1983 | Pratt, Jr. et al. | 128/92 R |

OTHER PUBLICATIONS

Oh, I.; "The Use of the Femoral Compactor"; *Orthopaedic Review;* vol. IX, No. 5; pp. 61–62 (May 1980).

Harris, W.; "Plugging Medullary Canal and Using a Cement Gun"; *Orthopaedic Review;* vol. IX, No. 5; pp. 75–78 (May 1980).

*Primary Examiner*—C. Fred Rosenbaum
*Assistant Examiner*—C. W. Shedd
*Attorney, Agent, or Firm*—Charles J. Knuth; Peter C. Richardson; Lawrence C. Akers

[57] ABSTRACT

A novel cannula is disclosed for use in the application of bone cement to the prepared intramedullary canal of a bone prior to the cementation of a surgical implant therein. The novel cannula comprises a hollow tube adapted to slidingly receive the nozzle of a bone cement extruder, an inflatable cuff surrounding the tube, and means to inflate the cuff. In operation, the inflated cuff forms a seal against the wall of the intramedullary canal, thereby preventing escape of cement through the open end of the prepared canal and insuring that the applied cement is properly pressurized within the canal. As a result, a highly secure cementation of the surgical implant within the intramedullary canal is achieved.

9 Claims, 6 Drawing Figures

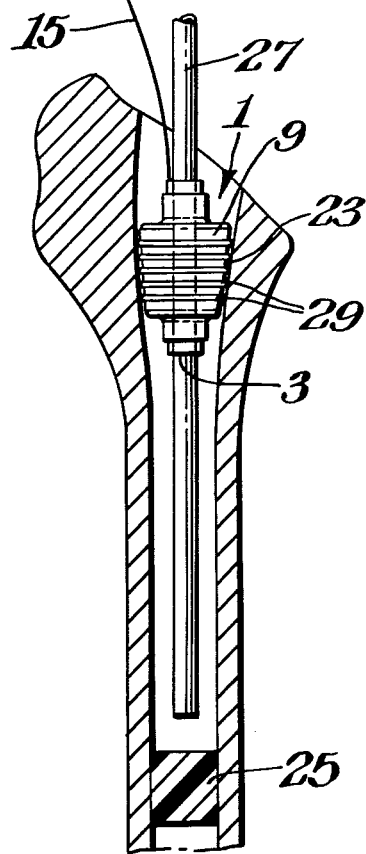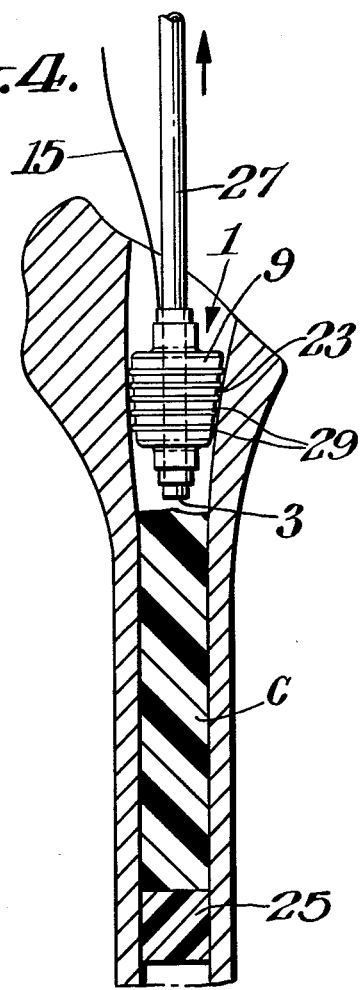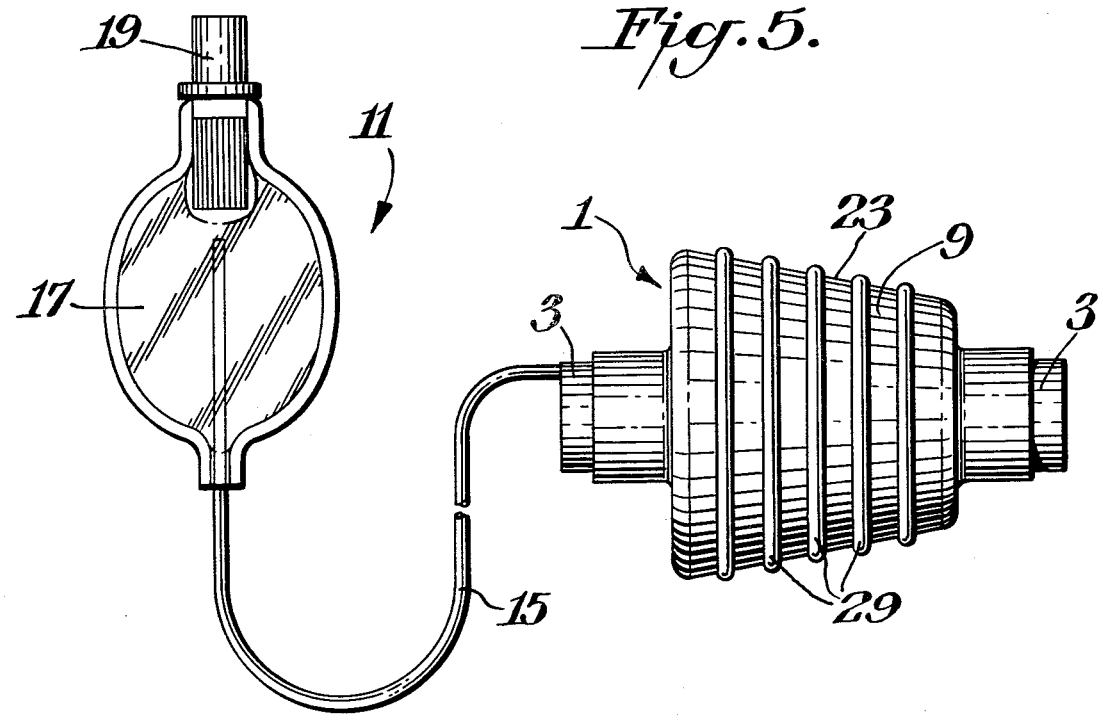

INTRAMEDULLARY CANAL SEAL FOR CEMENT PRESSURIZATION

BACKGROUND OF THE INVENTION

The cementation of surgical implants within the intramedullary canal of a patient's bone has proven to be a surgical procedure of great benefit to mankind. The most common example of this procedure is the implantation of a femoral prosthesis within the intramedullary canal of the femur. Polymethylmethacrylate bone cements, e.g. Surgical Simplex P Bone Cement (Howmedica, Inc.; New York, N.Y.), have been used with great success in this procedure. The bone cement is applied in a viscoelastic state into the prepared intramedullary canal with a bone cement extruder, after which the implant is inserted into the canal. The cement, which polymerizes and hardens in the space between the bone and the implant, functions as a luting agent. The quality of the fixation is greatly enhanced by the mechanical interlocking of the cement with the porous trabecular structure of the cancellous bone of the wall of the intramedullary canal and with any pores, dimples, elevations, keys, etc., provided on the surface of the implant.

Fixation of surgical implants with polymethylmethacrylate bone cements within intramedullary canals has been practiced with great success for many years. On rare occasions, however, problems associated with the premature loosening of the implant in use have been observed. One explanation for these loosening problems is an inadequate penetration of the bone cement into the cancellous bone of the intramedullary canal wall. It is known that this penetration can be improved by pressurizing the viscoelastic bone cement within the intramedullary canal so as to work the cement deeply into the cancellous bone of the canal wall before it hardens. Thus, it is well known to utilize an intramedullary plug to prevent passage of cement distally (with reference to the surgeon) of its desired location within the intramedullary canal (see, for example, U.S. Pat. Nos. 4,245,359; 4,276,659 and 4,293,962, and European Pat. No. 6408). Pressurization can be further improved to some extent by finger packing by the surgeon. Compactors have been used to compress and pressurize bone cement applied to an intramedullary canal. However, the use of a compactor requires the addition of a distinct, time-consuming step to the surgical procedure, with the results being operator intensive, i.e. the extent of pressurization achieved depends upon the axial force exerted by the surgeon. Additionally, it is known to equip the nozzle of a bone cement extruder with a non-inflatable restrictor (e.g. the Miller Bone Cement Injector Restrictor Set; Zimmer USA; Warsaw, Ind.) made of a resilient material to block the flow of cement between the nozzle and the bone through the open end of the prepared intramedullary canal. However, the quality of the seal obtained is limited because the fit of such a restrictor against the prepared bone is more in the nature of a line contact at the open end than a surface-to-surface contact and, furthermore, the quality of the seal will be reduced when the restrictor is unable to completely fill any irregularities in the bone against which it fits. Again, the extent of pressurization achieved depends upon the axial force exerted by the surgeon.

SUMMARY OF THE INVENTION

It is an object of the present invention to provide a simple and expeditious method for inserting bone cement into the intramedullary canal of a patient and reproducibly obtaining a high degree of pressurization of the cement within the canal, prior to the cementation of a surgical implant therein, which method eliminates or alleviates the difficulties encountered with the use of prior art techniques.

This and other objects of the invention are achieved with a novel method for inserting bone cement through the open proximal end of a prepared intramedullary canal of a bone and into said canal, and pressurizing said cement therein, comprising the steps of providing a bone cement extruder having a nozzle, providing a cannula comprising a hollow tube having a distal end and a proximal end, an inflatable cuff surrounding at least a portion of the tube, and means to inflate the cuff, with the tube being adapted to receive the nozzle in sliding fit, sliding the tube over the nozzle so that the cannula is held by the extruder, inserting the nozzle and the cannula through said open end into the intramedullary canal, inflating the inflatable cuff so that it forms a high surface area seal against the wall of said canal, and applying bone cement through the nozzle into said canal until said cement becomes pressurized, whereby escape of cement through the open end of the intramedullary canal is prevented by said seal. Preferably, the nozzle is slid in a proximal direction within the hollow tube, which remains stationary, as the bone cement is applied.

The scope of the present invention includes additionally the novel cannula used in the method of the invention. Since the cuff forming the seal is inflatable, it is adapted to closely conform to the contour of any irregularities in the surface of the canal wall, thus forming an excellent seal by preventing bypass of cement around the cuff in the region of said irregularities. Preferably, the inflatable cuff is permanently affixed to the hollow tube.

In a preferred embodiment of the invention, the inflatable cuff has a substantially frustoconical shape when inflated and is provided with a corrugated surface to fit against the wall of the intramedullary canal. Both of these features improve the seal formed by the inflated cuff.

DETAILED DESCRIPTION OF THE INVENTION

The invention will be described in detail with reference to a preferred embodiment thereof. Reference to this embodiment does not limit the scope of the invention, which is limited only by the scope of the claims. In the drawings:

FIGS. 3 and 4 illustrate the practice of the method of the present invention; and FIG. 5 is a side elevational view of the cannula shown in FIG. 2.

Figure 1:
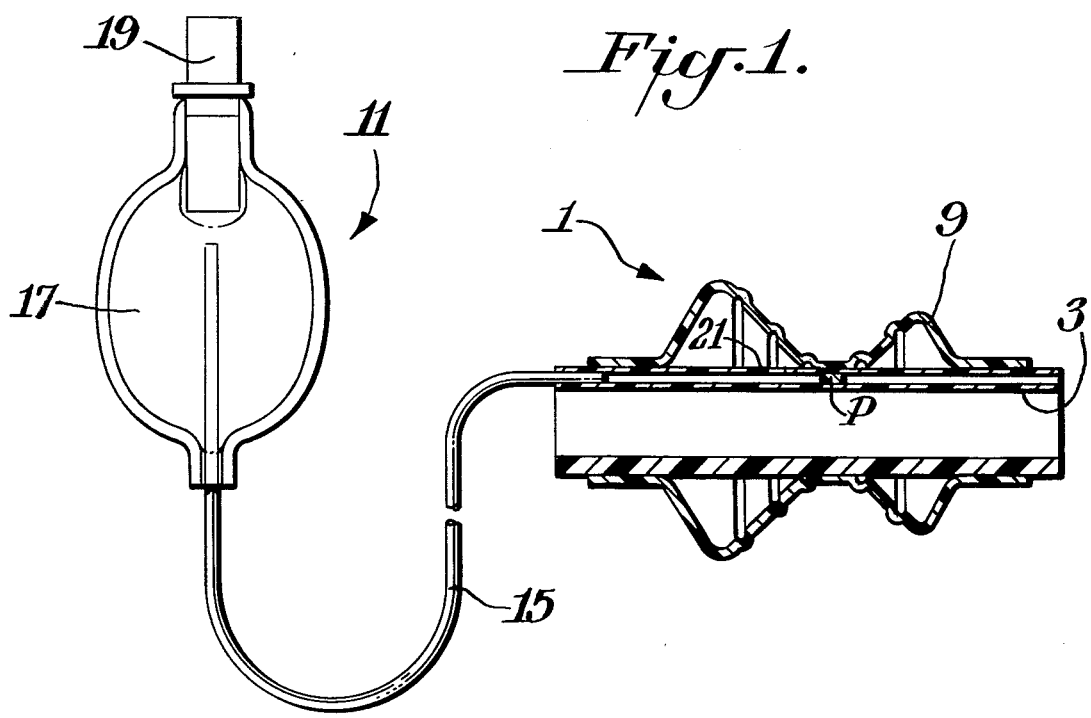
FIG. 1 is a side view of a disposable cannula for use in the present invention, with a portion of the cannula shown in section and with the inflatable cuff shown in the non-inflated condition.
Figure 2:
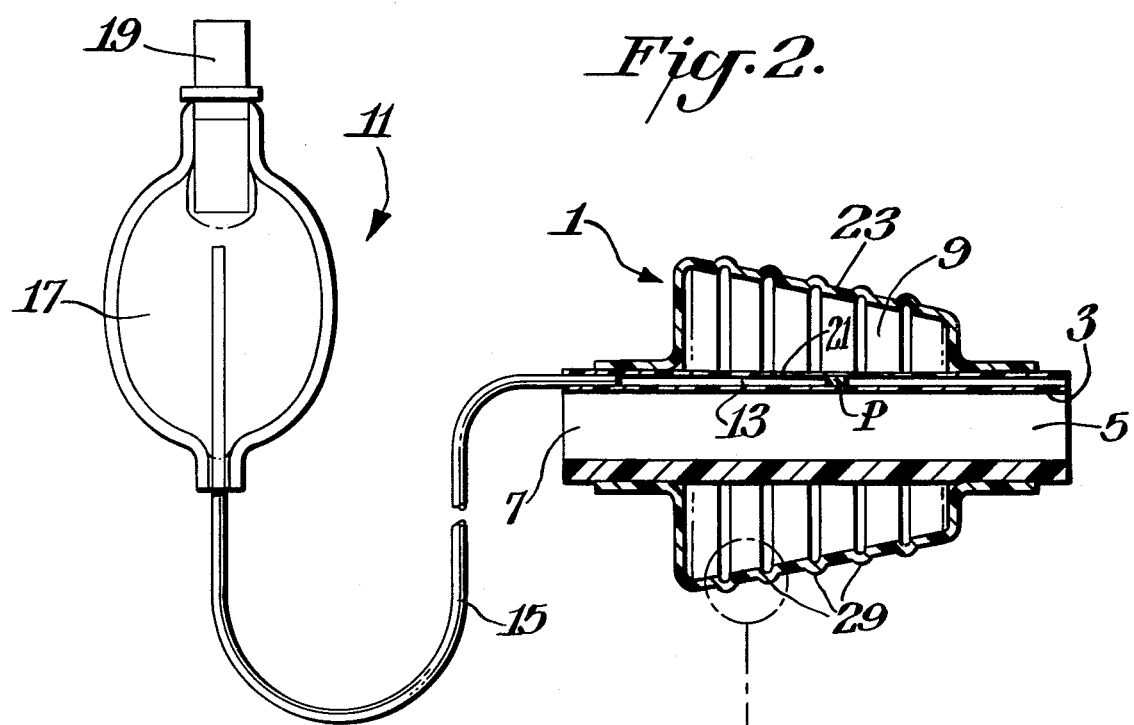
FIG. 2 is the same view as FIG. 1, after the cuff has been inflated.

A novel cannula 1 of the invention is shown in FIGS. 1, 2 and 5. Cannula 1 consists of a hollow tube 3 having a distal (with reference to the surgeon) end 5 and a proximal end 7, an inflatable cuff 9 surrounding tube 3 between ends 5 and 7, and means 11 to inflate cuff 9. Inflation means 11 comprises an inflation lumen 13 in the wall of tube 3, a fill line 15 sealed as its distal end to the proximal end of lumen 13, a pressure indicating bladder 17 in communication with the proximal end of line 15 and a self-sealing port 19 carried by bladder 17. The operation of the inflation means will be described later. Inflation lumen 13 communicates through aperture 21 in the wall of tube 3 to the interior of inflatable cuff 9 and is sealed distally of aperture 21, e.g. at location P. Cannula 1 is adapted to be used with a conventional bone cement extruder having a nozzle, typically a polyethylene tube, through which the cement is delivered to the patient. One such bone cement extruder is the Exeter Cement Gun (Howmedica, Inc.; New York, N.Y.). Preferably, tube 3 is also made of polyethylene. The inner diameter of tube 3 is slightly larger than the outer diameter of the extruder cement delivery nozzle so that tube 3 can receive the nozzle in sliding fit.

Figure 2A:
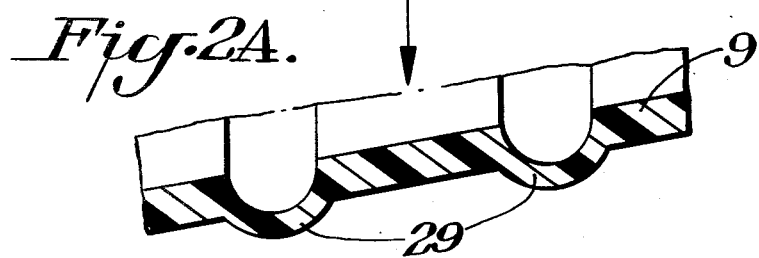
FIG. 2A is an enlarged view of a portion of the surface of the inflated cuff.

Inflatable cuff 9 is made of a thin, flexible and resilient material such as latex having a thickness of about 0.1 mm. It may also be made of, e.g., polyurethane or silicone rubber. It is permanently affixed by heat sealing at its distal and proximal ends to tube 3. The cuff may be designed to have any of a number of shapes when inflated, e.g., toroidal, cylindrical, oval, spherical. Preferably, as shown in FIG. 2, the cuff has a substantially frustoconical shape when inflated. Such a frustoconical shape will follow the general shape of the inner wall of the prepared intramedullary canal. Most preferably, the diameter of the proximal base of the frustum is about 1.5 times the diameter of the distal top of the frustum. The inflated e.g. latex cuff will closely conform to the contour of any irregularities in the surface of the canal wall. As shown in the figures, the surface 23 of the inflated cuff 9 that fits against the wall of the intramedullary canal is provided with a plurality of laterally-extending corrugations 29. These corrugations may be curved or wave-like in cross-section, as shown in FIG. 2A, or for example triangular, rectangular or square in cross-section. The presence of the corrugations on surface 23 improves still further the seal formed by the inflated cuff against the wall of the intramedullary canal. Cuff 9 may be made by known techniques, such as by film-casting or dipping, using a mandrel provided with the desired overall size and shape and the desired corrugations. Typically, the height of the corrugations is from about 10% to about 25% of the maximum cross-sectional diameter of the inflated cuff.

The method of the present invention will be described in connection with the cementation of a femoral prosthesis. It is to be understood that said method may also be employed in the cementation of implants in other long bones, e.g. the tibia or humerus. The diseased or damaged portions of the proximal end of the femur are removed, the bone resected and the exposed intramedullary canal cleaned, e.g. with a bone lavage and an intramedullary brush. The purpose of the cleaning operation is to prepare the intramedullary canal for cementation of the prosthesis therein by removing bone and tissue debris and blood clots to expose a substantial area of clean cancellous bone in the canal wall to interlock with the bone cement. An intramedullary plug 25 is then preferably inserted into the canal to prevent passage of cement distally of its desired location within the intramedullary canal. The bone cement is then mixed and loaded into the extruder according to the manufacturer's instructions. With cuff 9 not inflated, tube 3 is slid over the nozzle 27 of the cement extruder, preferably with the aid of a lubricant such as a silicone lubricant, and the nozzle 27 is inserted through the open proximal end of the prepared intramedullary canal until its distal tip is generally proximate to plug 25. Tube 3 is then slid along nozzle 27 until at least a portion of cuff 9 has been inserted through said open end. (Alternatively, tube 3 may be placed at its desired position on nozzle 27 before the nozzle is inserted into the intramedullary canal.) Cuff 9 is then inflated to form a seal against the wall of the canal (see FIG. 3). The cuff is inflated with a syringe connected to a three-way stopcock (not shown in the figures) having fill and release positions and in communication with port 19. The inflation fluid may be for example a pressurized gas, e.g. air, sterile saline or a sterile silicone oil. The inflation pressure is not critical but preferably, of course, is greater than the pressure to which the cement is to be positioned. The bone cement C is then applied through the nozzle, which carries cannula 1, into the intramedullary canal and, as the application continues, is pressurized within the canal, typically for from about 10 seconds to about 3 minutes at from about 1 psig to about 100 psig. Preferably, nozzle 27 is withdrawn through tube 3 from the position shown in FIG. 3 to that shown in FIG. 4 simultaneously with the application of the bone cement. The existence of the tight and secure seal formed by the fitting of surface 23 of cuff 9 against the canal wall prevents the escape of cement through the open proximal end of the prepared intramedullary canal and thus insures that a high degree of pressurization is achieved. The nozzle is then slid out of tube 3, the cuff is deflated by moving the three-way stopcock to the release position, the cannula is removed from the intramedullary canal and the femoral prosthesis is then inserted into the canal for cementation therein. Because of the excellent pressurization of cement resulting from the use of the present invention, the cement penetrates deeply into the cancellous bone of the intramedullary canal wall and a very strong and stable fixation of the prosthesis is achieved.

Variations of the above-described method that merely involve minor changes in the sequencing of steps are contemplated to be within the scope of the present invention. Thus, in one such variation, hollow tube 3 is first inserted into the intramedullary canal with cuff 9 non-inflated, the cuff is then inflated to form the seal against the canal wall, and nozzle 27 is then slid through tube 3. The critical feature of all such contemplated variations is that the cuff 9 is placed at its desired location in the intramedullary canal before it is inflated, so that upon inflation a high surface area seal of high quality is formed and the extent of pressurization achieved is not dependent upon the axial force exerted upon the cement extruder by the surgeon.

I claim:

1. A method for inserting bone cement through the open proximal end of a prepared intramedullary canal of a bone and into said canal, and pressurizing said cement therein, prior to the cementation of a surgical implant within said canal, said method comprising the steps of (a) providing a bone cement extruder having a nozzle;

(b) providing a cannula comprising a hollow tube having a distal end and a proximal end, an inflatable cuff surrounding at least a portion of said tube, and means to inflate said cuff, with said tube being adapted to receive said nozzle in sliding fit;

(c) sliding said tube over said nozzle so that said cannula is held by said extruder;

(d) inserting said nozzle and said cannula through said open end into said intramedullary canal;

(e) inflating said inflatable cuff so that it forms a seal against the wall of said canal; and (f) applying bone cement through said nozzle into said canal until said cement becomes pressurized, whereby escape of cement through the open end of said intramedullary canal is prevented by said seal.

2. A method of claim 1 wherein said nozzle is slid in a proximal direction within said tube as said bone cement is applied during said step (f).

3. A method of claim 1 or 2 wherein said inflatable cuff has a substantially frustoconical shape when inflated.

4. A method of claim 1 or 2 wherein at least a portion of the surface of said cuff that fits against the wall of said intramedullary canal to form said seal is corrugated.

5. A method of claim 3 wherein at least a portion of the surface of said cuff that fits against the wall of said intramedullary canal to form said seal is corrugated.

6. A method of claim 1 wherein said inflatable cuff is permanently affixed to said hollow tube.

7. A cannula for use in inserting bone cement into the intramedullary canal of a bone and pressurizing said cement therein comprising a hollow tube having a distal end and a proximal end, an inflatable cuff surrounding at least a portion of said tube, and means to inflate said cuff, with said inflatable cuff having a substantially frustoconical shape when inflated and unrestrained, and with said cuff being adapted to form a seal against the wall of said intramedullary canal when said cannula is inserted into said canal and said cuff is inflated.

8. The cannula of claim 7 wherein said inflatable cuff is permanently affixed to said hollow tube.

9. The cannula of claim 7 or 8 wherein at least a portion of the surface of said cuff that fits against the wall of said intramedullary canal to form said seal is provided with a plurality of laterally-extending corrugations.

* * * * *